United States Patent
Gasik et al.

(10) Patent No.: US 10,379,106 B2
(45) Date of Patent: Aug. 13, 2019

(54) IN VITRO METHOD FOR MEASUREMENT AND MODEL-FREE EVALUATION OF TIME-INVARIANT BIOMATERIALS FUNCTIONS

(71) Applicant: Seqvera Ltd. Oy, Helsinki (FI)

(72) Inventors: Michael Gasik, Helsinki (FI); Yevgen Bilotsky, Melbourne (AU)

(73) Assignee: Seqvera Ltd. Oy, Helsinki (FI)

( * ) Notice: Subject to any disclaimer, the term of this patent is extended or adjusted under 35 U.S.C. 154(b) by 182 days.

(21) Appl. No.: 15/655,331

(22) Filed: Jul. 20, 2017

(65) Prior Publication Data
US 2019/0025286 A1    Jan. 24, 2019

(51) Int. Cl.
| | |
|---|---|
| G01N 33/50 | (2006.01) |
| G01N 33/483 | (2006.01) |
| G01N 33/487 | (2006.01) |
| G01N 33/537 | (2006.01) |
| G01N 33/00 | (2006.01) |

(52) U.S. Cl.
CPC ..... *G01N 33/5008* (2013.01); *G01N 33/4833* (2013.01); *G01N 33/48792* (2013.01); *G01N 33/5375* (2013.01); *G01N 33/00* (2013.01)

(58) Field of Classification Search
CPC ........ G01N 33/4833; G01N 33/48792; G01N 33/5008; G01N 33/5375
See application file for complete search history.

(56) References Cited

U.S. PATENT DOCUMENTS

| | | | | |
|---|---|---|---|---|
| 6,107,081 | A * | 8/2000 | Feeback | A61B 5/1108 435/284.1 |
| 6,289,753 | B1 * | 9/2001 | Basser | G01N 13/04 73/866 |
| 6,772,642 | B2 * | 8/2004 | Hajduk | G01N 3/10 506/12 |
| 7,013,709 | B2 * | 3/2006 | Hajduk | B01J 19/0046 73/37 |
| 7,547,540 | B2 * | 6/2009 | Takagi | C12M 35/04 435/289.1 |
| 7,772,000 | B2 * | 8/2010 | Hauselmann | A61L 27/28 435/375 |
| 7,906,322 | B2 * | 3/2011 | Bergeron | C12M 35/04 435/284.1 |
| 7,945,964 | B2 * | 5/2011 | Wakiyama | G01Q 70/04 73/105 |
| 2002/0042701 | A1 * | 4/2002 | Dancu | G09B 23/28 703/9 |

(Continued)

OTHER PUBLICATIONS

Lujan, T. J. et al.: "A novel bioreactor for the dynamic stimulation and mechanical evaluation of multiple tissue-engineered constructs." Tissue Eng. C 17 (2011), 367-374.

(Continued)

*Primary Examiner* — David J Bolduc
(74) *Attorney, Agent, or Firm* — Berggren LLP

(57) ABSTRACT

The invention discloses a method for in vitro testing of specimens, such as biomaterials, to obtain history-dependent, time-invariant functional materials properties using time-convolution and idempotent analysis. The purpose of the method is to measure these properties using a data processing without limitations of materials models, the properties linearity or material homogeneity.

7 Claims, 5 Drawing Sheets

(56) References Cited

U.S. PATENT DOCUMENTS

| | | | | |
|---|---|---|---|---|
| 2005/0058842 | A1* | 3/2005 | Liebmann-Vinson | B82Y 30/00 428/447 |
| 2005/0239047 | A1* | 10/2005 | Gimzewski | G01N 33/5008 435/4 |
| 2005/0265980 | A1* | 12/2005 | Chen | C12N 5/0647 424/93.7 |
| 2006/0194261 | A1* | 8/2006 | Kim | G01N 33/5008 435/7.2 |
| 2009/0088342 | A1* | 4/2009 | Moraes | C12M 23/16 506/12 |
| 2010/0138163 | A1* | 6/2010 | Gallippi | A61B 8/485 702/19 |
| 2010/0284016 | A1* | 11/2010 | Teitell | G01J 3/453 356/451 |
| 2013/0160577 | A1* | 6/2013 | Williams | C12M 35/04 73/865.6 |
| 2014/0046183 | A1* | 2/2014 | Park | A61B 8/485 600/438 |
| 2014/0127795 | A1* | 5/2014 | Dancu | G01N 21/47 435/289.1 |
| 2014/0295538 | A1* | 10/2014 | Franck | G01N 3/08 435/288.7 |
| 2018/0328798 | A1* | 11/2018 | Silver | A61B 5/00 |

OTHER PUBLICATIONS

Martin, I. et al.: "The role of bioreactors in tissue engineering." Trends in Biotechnol. 22 (2004), 80-86.

Kasper, C. et al. (eds.): "Bioreactor systems for tissue engineering II: strategies for the expansion and directed differentiation of stem cells", in "Advances in Biochemical Engineering/Biotechnology", Springer, vol. 123 (2010), 330 p.

Hutmacher, D. W. et al.: "Computational fluid dynamics for improved bioreactor design and 3D culture." Trends in Biotechnol. 26 (2008), 166-172.

Pioletti, D. P. et al.: "Effect of micromechanical stimulations on osteoblasts: development of a device simulating the mechanical situation at the bone-implant interface." J. Biomech. 36 (2003), 131-135.

Shimomura, K. et al.: "Cyclic compressive loading on 3D tissue of human synovial fibroblasts upregulates prostaglandin E2 via COX-2 production without IL-1β and TNF-α." Bone Joint Res. J. 3 (2014), 280-288.

Mauck, R. L. et al.: "Functional tissue engineering of articular cartilage through dynamic loading of chondrocyte-seeded agarose gels." Trans. ASME, 122 (2000), 252-260.

Salvetti, D. J. et al.: "Design and validation of a compressive tissue stimulator with high-throughput capacity and real-time modulus measurement capability." Tissue Eng. C 18 (2012), 205-214.

Mohanraj, B. et al.: "A high-throughput mechanical screening device for cartilage tissue engineering." J. Biomech. 47 (2014), 2130-2136.

Dealmeida, M. F. et al.: "Self-similarity, symmetries and asymptotic behavior in Morrey spaces for a fractional wave equation." Differ. Integr. Equ. 25 (2012), 957-976.

Verotta D.: "Fractional dynamics pharmacokinetics—pharmacodynamic models." J. Pharmacokinet. Pharmacodyn. 37 (2010), 257-276.

Hanyga, A.: "Power-law attenuation in acoustic and isotropic anelastic media." Geophys. J. Inter. 155 (2003), 830-838.

Maslov, V.: "The characteristics of pseudo-differential operators and difference schemes." Actes Congrès intern. Math. 2 (1970), 755-769.

Marquez, J. P. et al.: "Thin bio-artificial tissues in plane stress: the relationship between cell and tissue strain, and an improved constitutive model." Biophys. J. 88 (2005), 765-777.

Baeumer, B. et al.: "Inhomogeneous fractional diffusion equations." Frac. Calc. Appl. Anal. 8 (2005), 371-386.

Gorenflo, R. et al.: "Analytical properties and applications of the Wright function." Frac. Calc. Appl. Anal. 2 (1999), 383-414.

Gerisch, A. et al.: "Robust numerical methods for taxis-diffusion-reaction systems: applications to biomedical problems." Mathem. Computer Model. 43 (2006), 49-75.

Gunawardena, J.: "An introduction to idempotency." HP Laboratories Bristol, Publication HPL-BRIMS-96-24 (1996), 50 p.

Luchko, Y. et al.: "Cauchy and signaling problems for the time-fractional diffusion-wave equation." J. Vibr. Acoust. 136 (2014), 050904.

Norris, A.: "Eulerian conjugate stress and strain." J. Mech. Mater. Struct. 3 (2008), 243-260.

Lubarda, V.A. et al.: "On the elastic moduli and compliances of transversely isotropic and orthotropic materials." J. Mech. Mater. Struct. 3 (2008), 155-170.

Xiao, H.: "Invariant characteristic representations for classical and micropolar anisotropic elasticity tensors." J. Elasticity 40 (1995), 239-265.

Verbruggen, S. W. et al.: "Fluid flow in the osteocyte mechanical environment: a fluid-structure interaction approach." Biomech. Model Mechanobiol. 13 (2014), pp. 85-97.

Huiskes, R. et al.: "Effects of mechanical forces on maintenance and adaptation of form in trabecular bone." Nature 405 (2000), 704-706.

Claes, L. E. et al.: "Magnitudes of local stress and strain along bony surfaces predict the course and type of fracture healing." J. Biomechanics 32 (1999), 255-266.

Milan, J. L. et al.: "Simulation of bone tissue formation within a porous scaffold under dynamic compression." Biomech. Model. Mechanobiol. 9 (2010), 583-596.

Sittichokechaiwut, A. et al.: "Short bouts of mechanical loading are as effective as dexamethasone at inducing matrix production by human bone marrow mesenchymal stem cells." Europ. Cells Mater. 20 (2010), 45-57.

Sladkova, M. et al.: "Bioreactor systems for human bone tissue engineering." Processes 2 (2014), 494-525.

* cited by examiner

IN VITRO METHOD FOR MEASUREMENT AND MODEL-FREE EVALUATION OF TIME-INVARIANT BIOMATERIALS FUNCTIONS

PRIORITY

This application does not claim priority of any other applications.

FIELD OF THE INVENTION

The present invention relates to a new method of testing materials, especially biomaterials, in vitro, allowing measurement and model-free evaluation of plurality of time-invariant material functions describing the behavior or performance of that biomaterial at proper clinically relevant conditions.

BACKGROUND OF THE INVENTION

It is now widely anticipated that the present level of evaluation of mechanical function in biomaterials and tissue engineering studies is highly insufficient. For example of 205 analyzed articles on cartilage tissue engineering, mentioning of applied mechanical stimulation, only 29% has some quantified material properties [1]. Correct and detailed biomaterial testing is rather time-consuming and expertise to properly quantify non-elastic material behavior of tissue is also scarce in many dedicated biology labs [1]. The unfortunate consequence is that little is currently known about how specific culture regimes stimulate functional growth [2].

One of the essential information lacking is transient physical maturation of biomaterials and tissue engineering constructs. Mapping the material properties could guide the development of effective culture protocols, being particularly important in the design of biodegradable materials, where the rate of degradation should coincide with the rate of new matrix formation [1]. The quality of information expected by the user of such methods should be not only sufficiently rigorous to provide scientifically based evidence on the material or tissue, but also to provide acceptable correlations, trends and predictions which can be safely used in design, development and applications of biomaterials.

Conventional mechanical testing or characterization of the material itself, usually involves determination of strength, hardness, fatigue, coatings adhesion strength, etc. as well as so called materials properties like elastic (Young) modulus, shear modulus, viscosity, loss tangent (for dynamic loading), etc. Many biomaterials, including those for implants, are being nowadays tested under different mechanical loading schemes, specified by various standards. Besides conventional (tensile, bending etc.) tests for materials themselves, there are also dedicated tests for implant materials such as fatigue tests (e.g. ISO 14801 for dental implants). These tests are targeting on determination of a few parameters only, such as tensile strength, high-cycle fatigue limit, and they are mostly destructive. Their main purpose is to determine the practical limits of materials in service conditions from mechanical point of view only. Standard mechanical tests do not usually involve any kind of biological factors. Here and later, only tests which do not lead to clear destruction of the specimen, i.e. non-destructive evaluation, are being considered.

The data quality reported for the same material might be also confusing, as no exact information is given for conditioning changes, and usually no solid proof shown e.g. about suitability of the small strain theory or material linearity [1]. Such conditions are often assumed by default, despite it is of common knowledge that "elastic modulus" cannot be uniquely defined for material which does not follow linear elasticity model.

Biocompatibility and other biological type in vitro tests evaluate biomaterials' ability to work in vitro, such as ISO 10993. Tests are being carried out in respective culture wells or similar devices with only goal to access the effect of materials (in direct contact or via an extract) on living cells in static conditions. There are many attempts of simultaneous application of biological objects (cells cultures) and movable materials specimens [3].

These methods might be roughly classified into two categories: various bioreactors and combined testing devices.

The purpose of the first ones (bioreactor based methods) is mainly to provide conditions for tissue cell culturing (tissue engineering applications such as growing tissue grafts), and the mechanical forces there are poorly controlled—rotating flask, perfusion cells, etc. [3]. As a result, realistic stresses and strain acting on the material are not possible to evaluate, and usually reported "fluid shear stress" or other such properties are roughly assessed as for fluid flow in some equivalent size channel system [4]. Such an approach is limited by the laws of physics as these stress and strains cannot be measured in principle, but only calculated (only real forces and displacements can be measured directly). For example, in [5], a device design is described to provide micromotions on the material in the presence of osteoblast cells. However, this device is not able to mimic host conditions at the bone/implant interface, because it does not include proper microfluidics or microstrains and therefore does not produce experimental results which are relevant in the present invention.

Furthermore, the conditions for known biomaterial testing methods usually are not compatible with proper tissue engineering and cell cultivation applications. For example, applied mechanical stimulus is known to cause cellular toxicity, involving multiple yet unclear mechanisms in bone cells. Also increase of mechanical strain has been shown to increase cellular toxicity in osteoblasts [6]. Thus bioreactors are in principle incapable to measure and quantify properties of the biomaterial itself, whether or not it is combined with the cells or living tissues.

To match cell culturing conditions with assessment of biomaterials several kinds of composite devices and methods have been reported. With these devices it is attempted to improve the situation by placing the material specimens into more biologically controlled environment (a closed chamber or the like) with simultaneous application of mechanical stimulus via feeding probes or grips. This is usually implemented within a mechanical testing machine, requiring a substantial modification to ensure that correct stimulus is indeed transferred to the material.

In one example [7] several cell-laden specimens are being loaded into a sample holder and dynamically compressed at prescribed pattern aiming on simultaneous measurement of bioactivity of the cells and elastic modulus of the specimens. As several specimens are loaded at once, no individual strain and stress control is possible, and the determination of the properties of the materials is based on fitting deformation curves to an arbitrary theory (such as biphasic model). As reported by the authors themselves [7], this theory has failed to describe behavior of these materials. In summary, this method and the apparatus require many assumptions, new theories or independent experiments to extract true material data.

In another example [1], the deformation stimulus was applied for every sample individually in a test battery, but the resulting force was not possible to measure, and hence stress values were only approximated after the experiments. Furthermore, application of small elastic strain model to materials which clearly do not follow this rule has lead to simplifications which decrease the quality and question the relevance of the data.

In yet another example [8], even more specimens were simultaneously subjected to prescribed loading, however, making it impossible to directly evaluate measurable data, as the signals required attachment of magnets and resistance sensors, requiring every time specific non-linear calibration to convert voltage drop into force.

Similar version of this method [9] was again directed on increase of number of specimens but failed to get strain resolution, control of strain differences between the specimens, and faced substantial non-uniformity of the deformation (as it was dictated by the tallest specimen). Final data analysis was based on assumption of the statistical "strength of control" which was reported to influence results criteria significantly.

In another example (US Patent App. 2005/153436A1), a servocontrolled bioreactor system is shown, designed especially for orthopaedic tissue engineering products, and the main purpose of which is to grow cells constructs. The description of this patent application also underlines that stiffness of the 'bioprosthesis' being tested should match the native tissue for all operating ranges or frequencies, which is impossible to have in practice.

In yet another example (US Patent App. 2014/0295538A1), a device and a system for mechanical measurement of biomaterial are disclosed. That device and the method is applicable only to transparent soft materials, as they employ digital image correlation in the volume of the specimen via microscopy techniques, based on displacement of embedded nanoparticle markers. Whereas the method may give exact specific displacements of the markers, it fails to determine mechanical properties as its application requires biomaterial elastic modulus to be known.

There are also other examples (US Patent App. 2012/035742A1, 2011/136225A1, U.S. Pat. No. 6,107,081), which outline such combined methods and devices having the cell and tissue culturing as the main objective. Such methods are unable to evaluate most of the properties of biomaterials (for instance, when a specimen does not have cells seeded, the application of these methods becomes obsolete). With or without the cell cultures, time-invariant properties of the biomaterials cannot be assessed in these systems.

All these methods have intrinsic flaws in measurement precision as none of them is able to subtract the supporting platen stiffness contribution, empty sample holder correction, temperature variations, or effect of the intermediate layers introduced (resistance sensors, adhesives, magnets, etc.). Increasing number of specimens must be paid off with less read-outs—for example, in method described in [9] only approximate elastic modulus was possible to measure.

A special group of methods aims on high-throughput screening of various biomaterials, where the application of mechanical stimulus is foreseen and some response of the material to that stimulus is being measured. For example, U.S. Pat. No. 9,043,156 discloses a method for monitored application of mechanical force to samples using acoustic energy and mechanical parameter values extraction using mechanical response models. This method is based on ultrasonic excitation, i.e. sonic wave propagation through an unknown material and measurement of that wave (signal) attenuation in time. Despite being a non-destructive evaluation method, it however fails to identify realistic properties of a material, as it requires many assumptions (speed of sound in the material, non-linearity of the attenuation coefficient, unknown correction factors, needed uniformity of the specimen and constant density, etc.). This method also does not utilize the wave propagation theory and therefore requires from the user a pre-selection of some mechanical model of the material before making any calculations. In this method, only elastic modulus, relaxation time and viscosity coefficient can be assessed in as much as they are linked to some pre-determined materials models. Change of the model would lead to different set of these values. This leads to large errors (about 50%) and necessity of additional experiments to determine initially guessed parameters is required for such calculations. Furthermore, this method does not teach how to process the data if many parameters are unknown and the material does not follow linear model or is clearly inhomogeneous. Moreover, use of ultrasound, even for short duration, causes some dissipation of the pulse power into heat, locally affecting the material being tested.

In another example US 2011/013758 similar method is disclosed, related to measurement of rheological properties of a material or a biomaterial. This method also uses ultrasound excitation, having the same drawbacks as the method of U.S. Pat. No. 9,043,156, but it aims on minimizing the need for parameters by using ultrasound excitation in two dimensions. With use of harmonic signal excitation and using complex Fourier transform, this method is limited to components of viscoelastic properties of flowing media only and at very high frequencies (close to sound speed range). Ultrasound test for such materials reveals different materials properties than low-frequency measurements which is more relevant for biomaterials in implants. The values obtained with any ultrasound-based method are not time-invariant ones, they do not incorporate history of loading (being useful for fluid materials) and they cannot characterize the material to the extent foreseen in the present invention.

Another method of high-throughput screening of a material with application of mechanical stimulus is disclosed in the US Patent Application US2009/0088342. This method simultaneously applies a force or displacement to an array of specimens located at flexible (polymer) membrane via adjustable pressure of a fluid on the other side of that force-transfer membrane. The method however, is only feasible for very small samples, such as for microsystems, requiring use of flexible and optically transparent substrates, bonding by an adhesive (which properties and contribution to the signal are not known), and uses a very simplified elastic theory for membranes deflection. This requires additional numerical modeling because the strain and stress distributions cannot be measured without assumption of linear elasticity of the material and the substrate at the same time. The reported observed errors in strain of 50-90% vs. average do not allow a unique determination of any relevant material property, as every specimen is subjected to a non-uniform stimulus and with unknown contribution from the device and substrate themselves.

In another example of U.S. Pat. No. 9,683,267, a method of in vitro testing of a specimen is disclosed, aimed on creation of a proper mechano-regulative index in the specimen by means of introduction of a controlled size orifice in the specimen test chamber to have respectively controlled fluid flow in and out of the chamber, where the fluid is further being analysed. However, this method requires prior knowledge of the specimen's mechanical properties such as elastic modulus, requires that the specimen deformation is purely elastic and assumes full linearity of the material behavior as otherwise the mechano-regulative index is not possible to calculate. Thus this method is incapable for measurement of specimen properties.

Yet another example in U.S. Pat. No. 6,772,642 presents a high-throughput mechanical testing device, used for combinatory screening purposes of two or more specimens at once. Its application, however, is limited to flexible polymer substrates and a very simple linear elastic theory for membranes deformation. This method is silent about the outputs in case the specimen is not homogeneous, if it behaves in a non-linear way and/or undergoes some transformations affected by the loading history.

None of known or above presented mechanical, biomechanical or combined methods is capable to measure and evaluate time-invariant properties of biomaterials (whether with cells as ATMP or as a part of hybrid products) simultaneously in one test from a single specimen. There is no single mechanical test which is able to get simultaneously a spectrum of time-invariant materials functions including e.g. aggregate modulus, slope modulus, dynamic modulus, alpha-value spectrum, viscostiffness spectrum, permeability, permittivity, characteristic times, intrinsic modulus and viscosity spectra, effective channel size for fluid transport, etc., without application of the fluid pressure gradient and without assumption of some simplified material model.

SUMMARY OF THE INVENTION

Accordingly, this invention provides solutions that none of the known disclosures are able to provide.

This invention addresses non-destructive testing of biomaterials for plurality of their properties, especially where these properties are functions of materials that depend on testing and environmental conditions, in the most cases, in an unknown way.

Furthermore, the invention also addresses obtaining time-invariant parameters of a plurality of these properties simultaneously with evaluation of the biomaterial specimens without application of models of pre-selected materials and without assumption of linearity of these materials. In addition, the objective of the invention is to use these properties to compare and assess performance of biomaterials where these natural properties of materials include their testing history.

It is an object of the present invention to provide a method for in vitro testing of materials, especially biomaterials, such as materials for preferential use in medical devices, ATMP (advanced therapy medicinal products) or hybrid products.

The inventors have experimentally discovered that properly controlled prescribed mechanical loading of a biomaterial specimen with measurement of resulting strain (or vice versa) via same single probe-sensor element can be used to evaluate true time-invariant biomaterial functions, obtained with time convolution (including loading history dependence) with idempotent analysis, without use of presumed materials models (such as elastic, hyperelastic, neo-Hookean, Mooney-Rivlin, etc.) and without need of complex Fourier transform, usually employed in dynamic mechanical analysis to get real and imaginary parts of the viscoelastic properties.

The inventors also found out that traditional complex algebra is not required to get these true invariant biomaterials parameters as it even might give a misleading knowledge of the materials properties and behavior.

The inventors have also experimentally discovered a way of linking and calculating other time-invariant properties related to fluid-material behavior, directly connected with material biological activity and possible clinical actions. This would enable to achieve test results capable to answer whether a biomaterial is good for its intended application as medical device or other product, how different biomaterials relate to each other in expected clinical performance, and how close the biomaterial specimen is to the properties of control specimen or natural tissue it aims to correct or replace.

According to the present invention, an in vitro test method for determining potential capability of a material or a device to perform in designated clinical conditions is provided. The methods of measurement and data analysis employed in the present invention do not require any prior knowledge about the material, its structure, or behavior. The test method comprises at least the following steps: positioning a material specimen onto a sample holder, immersion of the specimen and the sample holder into a fluid, establishing a contact of the specimen with a sensor probe (by moving the sensor probe until it contacts the specimen), applying a non-destructive mechanical stimulus to the specimen via the same sensor probe, measuring changes in a signal reflecting the specimen dimensions as function of time and applied stimulus parameters via the same probe, automatic subtraction of signal contributions from the background sources, inclusive of the sample holder, the sensor and the measurement device itself, processing these history-dependent measured data by time convolution without application of a material model, calculation of the specimen time-invariant material properties from these measured data, and optionally comparing the results with the reference or control specimen.

The test method may comprise inducing both mechanical forces (causing stress/strains) and biological/chemical stimuli to the test specimen, complemented with an autogeneous fluid flow adjacent to specimen surface (may be outside surface of the specimen or surface of pores in the specimen). According to certain embodiments the biological activity of the material vs. its environment can be determined.

The fluid media may comprise at least one of the following: gas, water, saline or buffered solution, simulated body fluid, extracellular matrix liquid, blood or blood substitute, designated cells culture, bacteria culture, virus culture, pharmaceutical or biological compound or any combination thereof. The fluid might be additionally adjusted and monitored by its biological, biochemical, chemical or physical features, such as chemical or biological composition, pH, temperature, viscosity, pressure, or flow velocity, when it has relevance for intended material application.

The main time-invariant material functions as an example are at least one of the following: aggregate modulus, specimen viscosity, intrinsic modulus, permeability, permittivity, slope modulus, dynamic modulus, dimensionless alpha-value, viscostiffness, fluid diffusivity, and characteristic times. Other similar properties and their time-invariant spectra linked with presence and concentration of chemical species, presence and status of the live species (cells, bacteria) or any changes of any of the above can be also employed, either separately or in a combination. In cases where material specimen swelling is present, the same method can be additionally used to evaluate swelling and swelling pressure of the specimen under controlled conditions.

One essential difference of the method of this invention vs. prior art is that permeability and permittivity of the material specimen are evaluated without application of the fluid pressure gradient from an external source. Another essential difference of the method is that mentioned time-invariant properties are calculated from the processed test data by time convolution without application of the Fourier transform, without use of conventional complex numbers algebra, and without an assumption of the material functional properties linearity. This does not exclude that the native signals from the measurement device could be filtered, smoothed or interpolated with Fourier transform but solely with the purpose of noise reduction.

The execution of the method and the data obtained also give possibility to evaluate kinetics of possible chemical, biochemical or biological reactions between the specimen and the surrounding fluid. Measuring reactions of the specimen may include determination of drug elution, agonism, efficacy, activity, or any combinations thereof (in the case of pharmaceutical applications). It may also comprise analyzing of cytotoxicity, cell proliferation and growth, cell differentiation, gene expression or inflammatory potential (for ATMP applications), or bacterial or viruses proliferation, growth and attachment (biofilm formation ability) or combinations thereof.

DETAILED DESCRIPTION OF THE INVENTION

Definitions

Figure 1A:
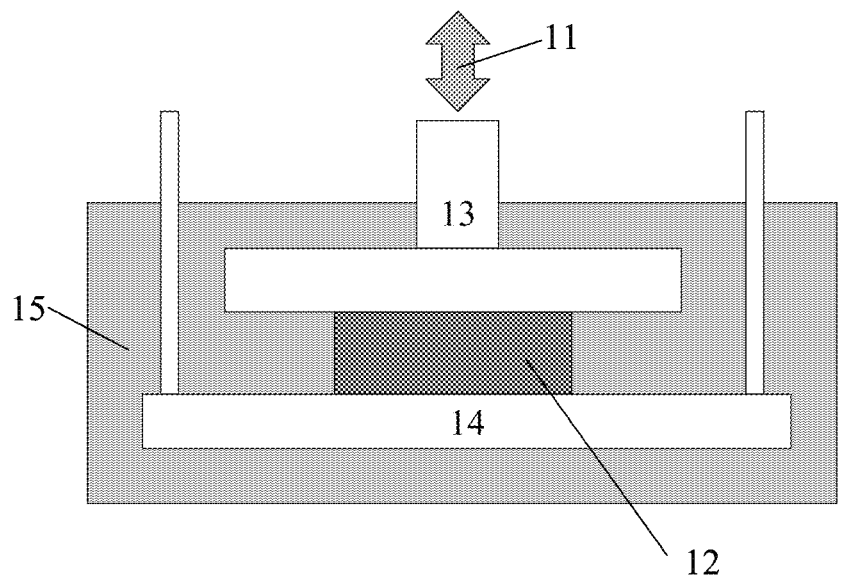
FIG. 1 presents the examples of the principle of the test method, in compression mode (FIG. 1A) and in bending mode (FIG. 1B)

For the reasons of clarity, the following definitions are used in this invention:

"Advanced Therapy Medicinal Product" (ATMP)—a biomedical product containing or consisting of engineered cells or tissues, and is presented as having properties for, or is used in, or administered to human or animal beings for regenerating, repairing or replacing a human or animal tissue.

"Aggregate modulus"—a time-invariant ratio of stress to true strain of the biomaterial, containing fluid or immersed in a fluid, at conditions when the average net fluid source in the specimen is nearly zero (quasi-equilibrium).

"Alpha-value" or "alpha parameter"—a time-invariant property of the specimen, having the value in the range between zero and unity, representing the viscous tendency of the material, even if the material itself is not a fluid. For transport processes like diffusion or wave propagation inside the materials and chemical reactions the alpha value range is between zero and two.

"Biomaterial"—a substance (other than a drug or living matter) or combination of substances, which can be used for any period of time, as a whole or as a part of a system which treats, augments, or replaces any tissue, organ, or function of the body of a human or an animal. Some typical examples of biomaterials are metallic alloys, polymers, ceramics, hydrogels, composites, and organic-inorganic hybrids, however it is to be understood that the list is not complete and that novel biomaterials are constantly developed and any and all of such biomaterials are included in the definition of the word in this application.

"Bioreactor"—a device or apparatus in which living organisms (e.g. cells, bacteria, fungi, organoids) synthesize desired substances or break down unwanted ones.

"Characteristic time"—a time-invariant measure of the material specimen at selected loading mode, being inverse to fluid mobility. It depends on combination of specimen size, porosity, permeability and fluid mobility (diffusivity)—the higher the characteristic time is, the slower is fluid movement at other equal conditions.

"Dynamic modulus"—a slope modulus defined as a ratio of dynamic stress amplitude and the dynamic true strain amplitude, and expressed in real (not complex) algebra.

"Fluid"—liquid or gas, either static or moving.

"High-throughput screening"—a method of evaluation or testing of a material aimed on simultaneous parallel gathering of the experimental data from an array of the specimens with the main goal to decrease number of testing time per specimen. High-throughput screening only can be used for a fast indication of whether a specimen fits some target or deviates from the limits set.

"High-output screening"—a method designed by the inventors for evaluation or testing of a material aimed on simultaneous parallel gathering and processing of plurality of experimental data from a single specimen, and which can be used for evaluation of the time-invariant materials functions.

"Hybrid product"—a biomedical product having two or more functions in the body (e.g. an implant (biomaterial) with addition of a pharmaceutical substance (drug) or living organisms (ATMP)).

"Idempotent analysis"—a method of mathematical analysis using operations substitution for linearization of a problem to be solved without alteration of initial variables, involving time convolution, observing causality principle (response always comes after the stimulus applied), respecting the boundaries of thermodynamics (no violation of conservation laws), and accounting for non-local effects. It differs from conventional mathematical analysis, where the derivative of a function is always local.

"Materials functions"—properties of a material which are not constants vs. applied mechanical stimuli "Medical device"—any instrument, apparatus, appliance, material or other article, whether used alone or in combination, intended by the manufacturer to be used for human beings or animals for investigation, replacement or modification of the anatomy or of a physiological process, and which does not achieve its principal intended action in or on the human or animal body by pharmacological, immunological or metabolic means, but which may be assisted in its function by such means.

"Non-destructive evaluation"—a testing method for a material specimen which does not lead to the destruction of the specimen. The specimen tested once could be tested again with the same method even if the specimen has undergone some irreversible changes.

"Permeability"—a quantified topological capacity of a material for transportation of a fluid through its porous structure. It only depends on material structure but not on fluid properties.

"Permittivity"—a quantified ability of a material to carry through its structure specific fluid.

"Slope modulus"—a derivative of the acting stress on the specimen by resulting true strain.

"Stiffness"—a quantity of a specimen to undergo certain deformation under applied prescribed loading.

"Stress"—a ratio of the acting force to the cross-sectional area of the specimen this force is being applied to.

"Time convolution"—a mathematical operation employing integration in time to obtain resulting average values of a property or a function.

"Time-invariant property"—a true (not imaginary or complex) property of a material, which may depend on other properties but does not depend explicitly on time or frequency of applied stimulus. Time-invariant property also includes specimen loading history data obtained by time convolution.

"True strain"—a specimen mechanical strain, calculated as natural logarithm of the stretch ratio (instant dimension to initial dimension).

"Viscostiffness"—a time-invariant quantified material function, reflecting link between stiffness and viscosity of the material, determined without assumption of the material model at chosen mode of loading. Together with the simultaneously obtained alpha-value is used to extract other time-invariant parameters such as characteristic time, moduli, permeability, etc.

Thanks to the employed test method according to the present invention, a combined biomaterials characterization is accomplished. The test method of this invention is an in vitro test, referring to a test performed outside a living body. The test method is non destructive, meaning that the specimen can be reused even if there are some irreversible changes during the first use. The test method of this invention comprises at least the following steps:

positioning a material specimen onto a sample holder absent fixation of the specimen, immersion of the specimen and the sample holder into a fluid, establishing a contact of the specimen with a sensor probe by moving the sensor probe until it is in contact with the specimen, applying a non-destructive mechanical stimulus to the specimen via the same sensor probe, this stimulus inducing the movement of the fluid inside and/or in adjacent to the specimen surface, measuring changes in the signal reflecting the specimen dimensions as function of time and applied stimulus parameters via the same probe, subtraction of signal contributions from the background sources, inclusive of the sample holder, the sensor and the measurement device itself, processing these history-dependent measured data by time convolution without application of a material model, calculation of the specimen time-invariant material properties from these measured data, and optionally comparing the results with the reference or control specimen.

The specimen or sample refers to a piece of a material to be tested, such as a biomaterial consisting synthetic, natural or modified natural materials intended to be in contact and interact with the biological system. Materials include at least but are not limited to ceramic, metal, polymer, composite and biological materials, such as an organ, a tissue or tissue engineered products (ATMP). The material may also include additional chemical, biological and/or pharmaceutical substances (a hybrid product), which may be integrated, embedded, or placed on the surface of the material as a coating. Preferably, the testing is used for materials, which are intended for use in interaction with body, also called as biomaterials.

Figure 1B:
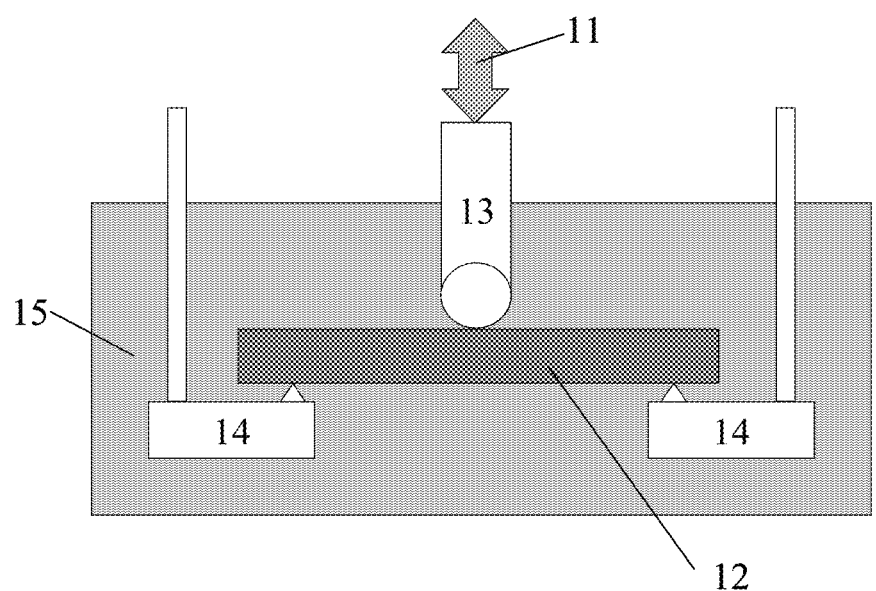

Referring to FIG. 1, in some example embodiments the test method comprises application of non-destructive mechanical force or displacement 11 to the test specimen 12 via the probe-sensor 13. Prior to testing the test specimen is positioned on the fixed support 14 any mechanical fixation (clamping or gripping), and the specimen's initial (reference) dimension is recorded after the probe 13 is moved to reach a contact with the specimen. Absence of mechanical fixation is of a particular importance of biological specimen, most of which cannot be reasonably clamped without affecting their properties. In addition, the test method comprises controlled fluid media 15, into which the specimen is at least partly immersed. The reactions of the specimen 12 with the fluid media 15 may be measured or monitored simultaneously or off-line with any known and feasible physical, biochemical or chemical method, providing that such measurements would not cause a significant or uncontrolled perturbation of the fluid properties such as chemical composition, density, viscosity, pH value, ionic stretch, osmotic potential. In other words, the test method allows combining testing of biological activity with mechanical loads (strains) and fluidics normally present at the body conditions, thus corresponding to more realistic situations, i.e. when the material is implanted into a living body (in vivo). It is evident for one skilled in the art that such test arrangement could be implemented in different ways.

The test method is essentially a non-destructive evaluation of the specimen, wherein the properties of a test sample are obtained without causing irreversible mechanical damage to the specimen. Since the method is non-destructive, it gives a possibility for post-examination the specimen on different levels, for example ex situ analysis of cells, bacteria or biofilms, or presence on concentration of pharmacological substances by any suitable known method. Additionally, this allows re-use of the same test specimen for subsequent tests, providing the testing history of the specimen is taken into account.

The test method also provides enhanced in vitro simulation of biomaterials, i.e. more efficient evaluation of a material in the conditions close to a hostile environment (in vivo). True time-invariant material functions could be evaluated for closer to clinically relevant environment giving higher confidence in expected materials performance and minimizing the associated application risks. In addition, the amount of in vivo tests or clinical tests required could be reduced, and also optimization of biomaterials design satisfying biomechanical and biomedical requirements will be achieved.

According to an embodiment, the method provides a combined material characterization, i.e. simultaneous measurement and calculation of plurality of material properties and functions, required to get an answer whether this material is compatible to the application and whether it is better or worse versus control or reference.

The key element of the data processing is based on time convolution and non-local, causal idempotent analysis [refs. 10, 11, 12, and 13]. This approach is completely different from commonly used materials laws (models such as elastic, viscoelastic or hyperelastic ones, like shown in U.S. Pat. No. 9,043,156), and complex algebra application (such as commonly used in viscoelastic analysis for estimation of storage and loss moduli). For biological systems one often cannot set up experiments to measure all of the state variables. If only a subset of the state variables can be measured, it is possible that some of the system parameters cannot influence the measured state variables or that they do so in combinations not defining the parameters' effects separately. It is well known that in general case such parameters are unidentifiable and are theoretically inestimable. Thus a common solution is normally to pre-select a linear model of the system, to guess initial estimates of the values of all parameters, and conduct experimental data analysis using that model [14]. The present method does not need such operations. The new method also uses integration with time convolution (global operation) instead of traditional differentiation (local operation), which stabilizes the calculation process and the output.

In brief, the data obtained from the probe-sensor, are digitized, recorded or stored in a form of computer file or as a part of a database. It is essential that analysis according to the present invention could be carried only after the physical test is completed, as time convolution cannot be made until all history data of specimen testing are collected.

The mathematical background of the invention is as follows. Experimental data are always functions of time (and sometimes spatial) coordinate. A parameter assessed (stress, strain, etc.) can be considered as a function of time $f(t)$ for some Banach space X. This implies that function $f(t)$ has its Laplace transform as the time convolution operation. The inventors recognized that besides time-dependence, a similar procedure can also be applied for spatial-derivative operators $L(f(x))$. For instance, L could be the generator of a convolution semigroup on $R^d$ defined by $$T(t)f(x) = \int f(x-y)\mu_t(dy) = \int f(x)p(x-y,t)dy, \quad (1)$$

where $p(x,t)$ is the density function of some probability measure $\mu_t$ on $R^d$ [15,16]. In practical applications, the Banach space X is specified as a suitable function space of real-valued (not complex) functions on some domain in $R^d$. For a time- or spatial coordinate dependence there is a function $u(t) \to T(t) \cdot f(x)$, which solves the Cauchy problem:

$$\partial_t \mu(t) = Lu(t); u(0) = f. \quad (2)$$

The equation system (2) has a general mathematical solution $$g(x,t) = \int q(x-y,t)f(x)dx, \quad (3)$$

where $q(x,t)$ is the convolution integral $$q(x,t) = \frac{t}{\alpha} \int_0^\infty p(x,s) G_\alpha(ts^{-1/\alpha}) s^{-1/\alpha - 1} ds, \quad (4)$$

$p(x,\$)$ is the Green's function solution to problem (2), and $G_\alpha$ is a probability density function called the stable subordinator [15,16]. The values of alpha-parameter in equation (4) must be non-negative to ensure causality principle. The values more than 2 represent unphysical situation where any time-dependence decays so quickly that the system becomes static and solved with a known art. When alpha-value is approaching zero or unity, the system of equations converges to standard linear mechanical visco-elastic equations which can be solved directly. The values between 1 and 2 are seldom occurring in practice, usually for the systems with non-conventional behavior and for waves propagation. The remarkable feature is that equations (3) and (4) can be always numerically explicitly computed without need of assumptions of functions linearity or being of some specific type.

Depending of the mode of testing (loading), specimen size, geometry, set testing objectives, one or another set of data is retrieved, converted and processed with a computer algorithm. Some algorithms and codes are known [17,18, 19], however they are not suitable for the present invention, as they do not foresee extraction of the time-invariant materials functions. The present method might be implemented in one or another dedicated computer code or software which specific precision, efficacy and processing time might be chosen depending on the problem addressed and number of the data points to be treated.

Before application, measured data must be converted after completion of the experiment (not during its execution). Especially strain data must be converted into true strain. The application of true strain in this method is justified as it is the only measure having solid thermodynamic grounds among other possible strain forms [20,21,22]. Here the true strain is calculated for quasi-static loading conditions as $$\varepsilon_{stat} = \left| \ln\left(1 + \frac{\Delta L}{H_0}\right) \right|, \quad (5)$$

and for dynamic loading conditions the equation was derived by the inventors as $$\varepsilon_{dyn} = \frac{1}{2} \ln\left(1 + \frac{2a_{dyn}}{H_0 + \Delta L - a_{dyn}}\right), \quad (6)$$

where $H_0$—initial dimension (such as height) of the specimen before the test, $\Delta L$—instant value of change of the height, $a_{dyn}$—amplitude of the dynamic displacement. In the equation (6) the change in the specimen dimensions during the test is incorporated and the non-symmetry of the harmonic signal is included.

The data analysis is taking into account that the knowledge of the full past of a given system does not in general uniquely determine the future development of the system. Hence an observed behavior of the specimen in the future may be a result of different histories (the inverted bifurcation theory, known as the "butterfly effect": despite an identical behavior in the past, a minimal parameter change may cause a drastic change in the future development of a system). Therefore, after the test history, data have to be accumulated to make non-local idempotent processing meaningful. This new generic algorithm procedure according to the present method is depicted in FIG. 2 flow chart, and it includes as least:

analyzing the experimental data file 21 structure, determination of the data content and variables (data parsing 22) into prepared data 23, possibly checking 24 by user interference 25 if the parsed data are correct, converting the parsed data 23 into working variables 26 such as real displacement into true strain according to (1) and (2), segmenting the variables 26, if needed, by experiment time, frequency, stress, true strain, etc. parameters, setting the experimental variables 26 and processing them by iterative time convolution 27, optionally checking 28 by user interference 29 if the convoluted data are correct, and back iterating if they are not, executing idempotent analysis 210 onto working variables, checking quality and errors of the procedure and re-iterating if necessary, calculation of true time-invariant variables (parameters 211 from this analysis 210 according to equations (3) and (4), recording the results 211 into a computer file 212 in parallel, displaying or otherwise reporting the results 211 in tabular, graphical or any other suitable form for selection 213, finishing the procedure by generating final results 215, with eventual interactive approval by the user 214.

Specific details of the algorithm used and method of analysis are depending on the modality of the test and shown below in examples in more detail. For one skilled in the art it is also evident that some steps in the above procedure could be amended or skipped, for example when initial data file 21 is already pre-processed so it could be fed directly into step 27 or 210.

Figure 2:
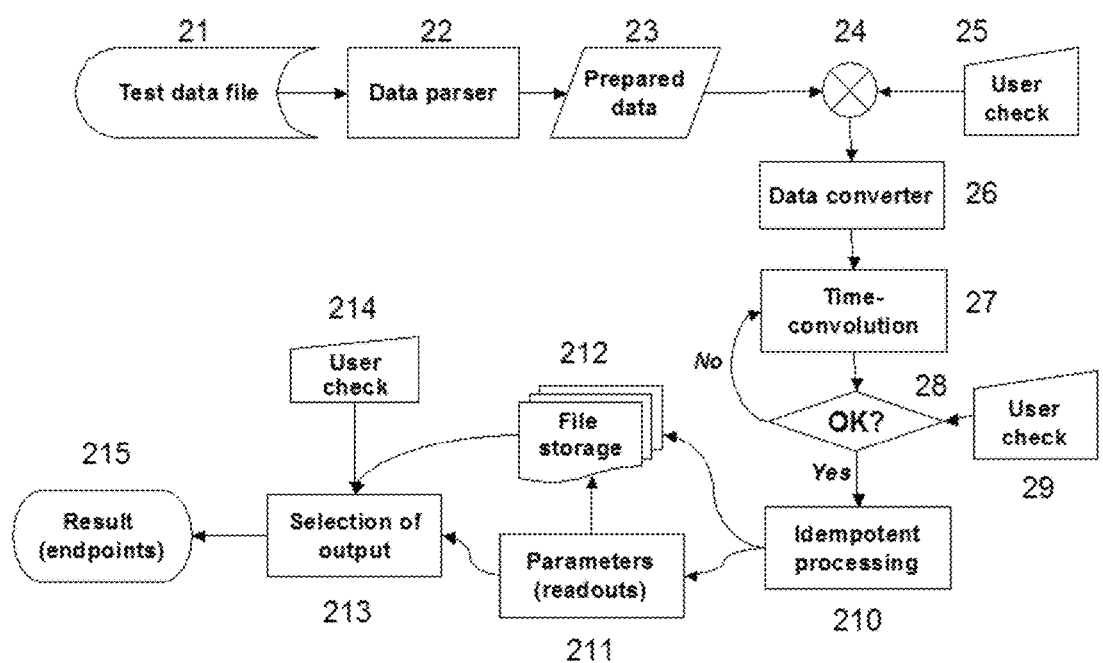
FIG. 2 presents a flow chart showing the principle of the test data processing.

Another essential feature of the analysis according to FIG. 2 is the targeting on time-invariant properties determination rather than presentation of time-dependent data. Obtaining time-invariant properties is an important objective in solid mechanics, as it would allow forecast of the material specimen behavior in time beyond the limits of practical experiment [20,21,22]. The practical effect of time-invariant properties in the method of the invention is that it allows long-time prediction of the biomaterial behavior.

Yet another essential feature of the above analysis is the comparison of these time-invariant properties with other specimens or with the control (reference) specimen. This minimizes the risks caused by determination of absolute values at two different time scales. Whereas the comparison can be also carried out for any other measurements, here mapping the time-invariant property A (like viscostiffness) to another property B (like alpha-value) reveals hidden trends in materials biomechanical behavior, which were discovered by the inventors experimentally (as shown below in the examples). These trends might be compared to the reference or target tissue to evaluate how close the test specimen is to this reference or tissue it is supposed to work with.

Measurements of material characteristics, such as reactions of the specimen with the surrounding environment may include analyzing of the media in situ during the test procedure, periodically or in parallel. The analysis with e.g. pharmacological relevance may comprise determination of a drug or a substance elution, efficacy, activity, or any combinations thereof, relevant to the intended specific drug or substance purpose. If live cells, bacteria, virions, tissue samples are added to the test systems, analysis may also comprise evaluation of dynamic cytotoxicity, cell proliferation and growth, cell differentiation, gene expression, or any relevant combination of the parameters of interest. Analysis may also comprise measuring of biofilm formation, using bacterial cultures with or without additional components, cultures and/or additions.

The main tests parameters (mode, force, displacement, time, frequency, sequence, geometry, fluid, temperature, etc.) can be modified in order to simulate different clinical cases or specific environments. The mechanical stimulus essentially comprise of bending, compression, shear or any other similar methods or their combinations, which do not require explicit mechanical fixation of the specimen in grips, depending on the material application purpose. The reason for not applying fixation grips is that for many biomaterials and tissues results are strongly depending on the fixation method, clamping force and respective preconditioning thus putting every specimen into different starting position.

The mechanical stimulus has a predetermined intensity, sequence, amplitude, frequency and duration. Also on the contrary to commonly used, this stimulus does not need to be elastic, only being a non-destructive one. The indentation method, often used for tissue analysis, is not recommended, as this procedure causes severe local deformation involving shear, inelastic flow, compression and tension in a mixture which cannot be reasonably described by a theory in a consistent way.

According to some embodiments, mechanical stimulus comprises providing a predetermined non-destructive force to the specimen or predetermined deformation with the goal of creation of a true strain and the displacements in the test specimen close to levels and motions relevant for the intended biomaterial purpose. Thus, the mechanical stimulus mimics both microstrains and the micromotions of the test specimen, similar to those occurring when the material is being implanted in a human body.

Thanks to the test method according to the invention, the stimulus naturally creates (auto-induces) microfluidic flow and micromotions inside or adjacent to surface of the specimen without need of external control of the fluid e.g. by a mechanical pump, without a presence of a calibrated orifice, or without any similar method, aimed on creation of fluid shear stress. In the present invention more realistic test results correlating with implant conditions may be achieved. In addition, studies relating to e.g. drug release or elution and its impact on biological response of the tested material may be connected to mechanical stimulus and auto-induced fluid flow.

In the test method the fluid may include, for example, gas, water, saline or buffered solutions, simulated body fluids, extracellular matrix liquid, blood or blood substitute, designated cells, bacteria and/or viruses cultures, pharmaceutical and/or biological compounds (such as but not limited to drugs, carriers, serum, factors, proteins, DNA, RNA, enzymes, etc). Cells may include, for example, mesenchymal stem cells or cancer cells, bacteria, and, in a wider sense, other biological objects like fungi, protozoa, archea, parasites, and others which are not strictly cells in a biological classification.

According to an embodiment, the liquid media constitution allows creation of any relevant combination of acting stimuli to evaluate required biomaterials performance in question. For example, application of simulating body fluid, simulated synovial fluid or simulated uterine fluid allows respectively materials behavior for orthopaedic cases, articular cartilage repair or intra-uterine devices tests. If bacteria are also injected in the media, competitive effects of cells and bacteria adhesion and proliferation might be evaluated at the same time. Such studies might be composed of any reasonable complexity.

According to the present invention, the environment conditions, such as surrounding atmosphere, of the test process are also controllable. For example, temperature for articular cartilage repair materials may be 25-33° C. in the presence of synthetic synovial fluid with 1-4 mg/mL sodium hyaluronate under air with 5% $CO_2$. In some cases, pH of the liquid media may be constant (buffered solution) whereas in other cases it might be deliberately changed during the test. The combination of these parameters is selected on the case basis depending on the tests objectives.

In addition to biomechanical strain, fluid velocity inside and in the vicinity of the specimen is an important factor for tissue formation and for the biomaterial/tissue interface. It also affects biofilm formation in the case of bacterial interactions, as the fluid flow plays an enormous role in all biological systems metabolism and proliferation. Thus, a combination of the naturally driven (autogeneous instead of caused by an external pump or other source) fluid flow at certain levels of mechanical stimulation is an important feature of the test method to be controlled. This presents a different concept compared to commonly used fluid shear stress, usually employed in perfusion bioreactors, as the real fluid shear stress cannot be in principle measured and it is definitely non-uniform inside a material specimen.

Advantages of the New Method

The present test method has essential differences from all known mechanoregulative theories [23,24,25,26] or from other prior art of testing of biomaterials in a fluid flow chambers or combined bioreactors [27,28]. These differences and advantages are as follows.

First, the method according to the present invention does not stipulate that the material has to be compliant with some pre-selected physical model (e.g. elastic, viscoelastic—Kelvin-Voigt, Maxwell, Burgers, Prony series, standard linear solid; hyper realistic, neo-Hookean, Mooney-Rivlin, etc.), and does not need extra assumptions or measurements of e.g. material Poisson ratios, attenuation coefficients, speed of sound, etc.). Selection of the material model in any combination, is obligatory for any conventional calculations in viscoelastic analysis or in numerical computer simulations like finite element methods or computational fluid dynamics, leading to the next step of selection or assumption of the set of biomechanical constants of the material, following these constants evaluation via experimental or modeled fitting of the data to some chosen equations. Whereas the present method can also determine conventional elastic modulus or stiffness of the material specimen, it is not the aim of the invention, as these parameters, usually required by the selected material model, are not generally time invariants and they are not used in the present analysis.

Second, the present method does not require the specimens having internal homogeneity unless it is the purpose of the material to be homogeneous. Variations of specimen local properties are not an obstacle for the testing and data analysis according to the present invention.

Third, the signals of force and displacement are coming out via the same probe sensor acting on the specimen (no separate sensors), and they are not being processed with complex algebra (Fourier transform) for obtaining real ('storage') and imaginary ('loss') parts of the material biomechanical properties. Instead, these signals are being directly recorded during the test and further analyzed by time-convolution and idempotent data processing methods to result into the time-invariant properties, which are the true properties of the material, not linked to any theory or assumption.

Forth, the experimental viscostiffness obtained with the present method does not require additional tests to be decomposed into true material functions, neither it demands modeling assumptions to make such decomposition.

Fifth, data analysis does not require that applied stimulus signal have some specific waveform (sinusoidal as in dynamic mechanical analysis or rheology) and thus can be applied to any arbitrary one, including non-harmonic oscillations, ramps, stepwise etc., in any sequence.

Sixth, the final results of analysis are determined solely by experiments and do not rely on known, assumed or pre-selected mechano-regulative models or requirements which specify certain limits of strain, strain rate, fluid velocity as independent variables. New method overrides needs of mechano-regulative indexes, elastic potentials, strain energy densities, etc.

Additional Embodiments of the Method

According to an embodiment, the test method may be additionally used for simultaneous measuring of a drug or a substance elution, drug efficacy, activity, potency, or any other combination, when the drug is located inside the specimen, on the surface of the specimen or deliberately added to the fluid surrounding the specimen. The drug elution or release analysis may be performed on-line from the media for instance aliquot off-samples necessity could be eventually eliminated with see-through spectrometry (IR, UV, Raman or the like). This analysis might be more accurate and sensitive to minor oscillations of the drug activity or cell population control than commonly used methods of liquid or gas chromatography, atomic adsorption spectroscopy, immuno-fluorescent microscopy. The analysis does not exclude existing methods as fluorescent microscopy, which can be applied after the test. All these analytical techniques are optional to the present invention.

In many cases, presence of living media, its metabolism and activity are hiding the real kinetics of drug elution and activity. It is also possible to measure pure physical-chemical effects (such as drug elution form porous substrates under applied mechanical loads but without added living media) and also pharmacological effects. New benefits of the present invention are in the idempotent data analysis, as the solution by equations (2-4) for pharmacologic kinetic equations is exactly the same as for biomechanical features. Such analysis may be included in the whole data processing chain depicted in FIG. 2.

According to an embodiment, the test method may be used for implant biomaterials for optional simultaneous measurement of their other properties, such as biocompatibility, bioactivity, or cytotoxicity at conditions closest to realistic applications. In addition, the pharmacological activity of the drug-laden implant materials may be measured. Further, in vitro cells proliferation and growth, differentiation, gene expressions, inflammatory potential and other parameters may be measured with optionally connected instruments, e.g. by a cell counting using external light diffraction, flow cytometry or photon correlation spectroscopy methods.

In the present invention it is also possible to combine tests with "ideal" living environment in vitro and in the "contaminated" non-sterile media to which specific cells (co-cultures), drug-resistant bacteria (*S. aureus, S. epidermidis, K. pneumonia*) and other micro-organisms (cross-cultures)

or even viruses, added to the fluid media or/and to the material, and being evaluated on parameters like cell adhesion, proliferation and growth under the proper mechanical stimulus instead of static soaking of a specimen in a culture well. The combined biomechanical stimulus imposed on the test specimen is similar to that existing in the living body. These measurements can be done within the measurement device or externally, and these data later correlated with the time-invariant properties obtained by the method of this invention. Application of the idempotent methods (equations 2-4) will result in the same framework of solutions, where only starting functions are different for different test scheme.

The method may also be applied to study for instance biofouling processes in chemistry, environmental and other similar applications, where the specimen is not specifically a biomaterial, a tissue sample or an implantable material (catheters, in vitro devices, analytical devices such as bio-MEMS, part of an apparatus, and numbers of others).

Example 1

According to this example, porous (~90%) scaffold specimens made of poly-L,D-lactic acid of fiber diameter of ~20 µm and external dimensions (l×w×h) (7±0.5)×(7±1)×(2±0.4) mm were positioned on the sample holder plate according to FIG. 1-A, and brought into the contact with the probe sensor of 15 mm diameter using compression mode sample holder in the dynamic mechanical analyzer DMA242C (Netzsch Gerätebau GmbH, Germany), with only raw data used (no complex transform). Tests were carried out at 25±1° C. and normal atmospheric pressure in air, using 30 mL of distilled water as fluid media. The precise size of each specimen was measured with non-contact optical method (±0.5 µm) with laser micrometer (Metralight Inc., CA, USA).

After letting the probe to establish the contact with the specimen and taring the offset, the starting height of the specimen immersed in media was again measured and used further as the starting height for true strain calculations (equation 5). For these tests, creep mode was chosen and was performed at different target loads (0.005-0.800 N; resolution±0.0005 N). It was noted that too low force caused specimens to swell if they have been kept wet before the test, and minimal force of 0.05 N during 15 min period of equilibration was experimentally found to keep zero dimensional changes before applying the target force. This allowed to estimate the swelling pressure (swelling potential) of this material in water to be 1.23±0.15 kPa.

Figure 3:
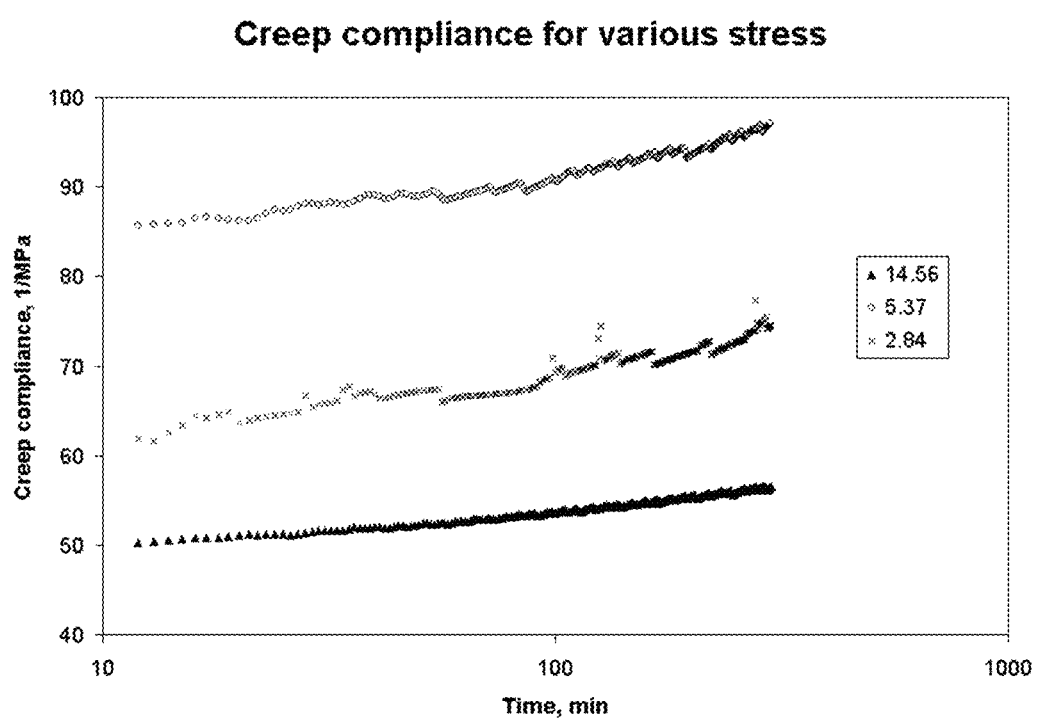
FIG. 3 presents the experimental data of the specimen shown in the example 1.

All tests were done up to 300 min (until dimensional changes were approaching constant values; displacement resolution±0.0005 µm). These data were stored and exported as ASCII text file into data processing software (Microsoft Excel complemented with customized code). The non-linearity of the applied force and associated change of deformation was taken into account numerically. The primary data were converted into stress and true strain (equation 5), and the ratio of strain to stress vs. experiment time. The creep compliance data, defined as the ratio of true strain to applied stress are shown in FIG. 3 for three acting stresses (expressed in kPa). It is seen that creep compliance clearly depends not only on experiment time, but also on the level of applied stress. An interesting experimental observation is that the creep compliance value is not in fact proportional to the applied stress (FIG. 3), indicating that material behavior is probably non-linear.

After that, numerical algorithm of time convolution was applied and processed data were non-locally integrated pair-wisely, row by row. Resulting values were tabulated as shown in Table 1 three different specimens at three different creep stress levels.

TABLE 1

Results of time-invariant parameters obtained in Example 1 as function of applied stress (kPa).

| Applied stress kPa | Alpha — | Visco-stiffness kPa · s$^\alpha$ | Slope modulus kPa | Characteristic time sec | Effective permeability nm$^2$ | Effective fluid diffusivity mm$^2$/s |
|---|---|---|---|---|---|---|
| 14.56 | 0.0322 | 24.8 | 21.4 | 101 | 7128.5 | $1.720 \cdot 10^{-1}$ |
| 5.37 | 0.0336 | 14.8 | 10.1 | 84536 | 24.23 | $2.759 \cdot 10^{-4}$ |
| 2.84 | 0.0431 | 21.3 | 10.4 | 16327351 | 0.113 | $1.323 \cdot 10^{-6}$ |

The practical value of these results is explained as follows. For this loading case (creep), the theoretical idempotent solution (equations 2-4) of the behavior of the materials predicts the power-law formal dependence of strain vs. time, even if there would be some damped waves propagating through the material [17,18,26]:

$$\varepsilon_{stat}(t) = \frac{\sigma_{stat} t^\alpha}{C_\alpha \Gamma(1 + \alpha)} \quad (7)$$

where $\sigma_{stat}$ is the creep stress, $C_\alpha$ is the viscostiffness, $\Gamma(\bullet)$—gamma-function, $\alpha$—alpha-parameter. As seen from FIG. 3, there is indeed a very good trend of creep compliance with the power law of time (i.e. linear vs. logarithm scale of time), giving the global value of $\alpha$ and the viscostiffness (table 1).

The inventors have discovered that numerically obtained time convolution shows clear changes in viscostiffness values vs. alpha-values for every integration time step. This allowed catching the behavior of the materials and extracting time-invariant slope modulus, characteristic time and other parameters (table 1). In general there is no explicit mathematical formula written as the calculation is iteratively progressing. Knowing that characteristic time (table 1) is inversely proportional to autogeneous (self-generated) fluid mobility (as in solid matrix only fluid moves in and out), and that in unconfined compression dimensional changes are linked with this fluid source and porosity changes, it is possible to access effective fluid diffusivity (table 1). For slow and globally laminar fluid flow, use of these values in conventional fluid dynamics equation (nearly incompressible Navier-Stockes fluid flow) has resulted also in effective permeability value (table 1).

From the experimental data FIG. 3 and Table 1 it is seen that there is no clear dependence of alpha-values and viscostiffness with applied stresses, neither clear proportional variation of slope modulus. However, it is quantitatively proven that higher stress level leads to more efficient removal of fluid from the sample, leading to characteristic time by several orders of magnitude less than in the case of smaller stress.

This method has allowed quantification of effective permeability (higher for higher stress) and fluid diffusivity (lower for lower stress). As the material is intrinsically hydrophobic, its clinical application for higher stresses would lead to a fast fluid extrusion which could be dangerous for cases like articular cartilage as material dry-out would lead to excessive wear and cells death. The biomaterial developer can now make a decision, which material conditions would be considered sufficient to keep fluid inside for sufficiently long time.

The results of Example 1 also demonstrate the "butterfly effect": small changes in alpha-values, viscostiffness and slope modulus for these tests indeed have lead to huge variations in fluid mobility. This is not possible to recognize with the existing state of the art.

Example 2

According to the second example, hydrogel specimens made of water and sodium hyaluronate (90 mg/mL) cross-linked with BDDE (1,4-butanediol diglycidyl ether) of dimensions (d×h) as (14±1)×(7±2) mm were positioned on the sample holder plate according to FIG. 1-A, and brought into contact with the probe sensor of 15 mm diameter using compression mode sample holder in the dynamic mechanical analyzer DMA242E "Artemis" (Netzsch Gerätebau GmbH, Germany), with only raw data used (no complex transform). Tests were carried out at 25±1° C. and at 36±1° C. and normal atmospheric pressure in air, using 30 mL of distilled water as fluid media. The precise size of each specimen before the test was measured with non-contact optical method (±0.5 μm) with laser micrometer (Metralight Inc., CA, USA). After letting the probe to establish the contact with the specimen and taring the offset, the test was executed and repeated 10 times by stepwise application of dynamic deformation amplitude from 5 to 50 μm at 1 Hz (displacement resolution±0.0005 μm). No swelling was observed for specimens during equilibration and no interaction of the specimen with the fluid media was detected.

Similarly to Example 1, the data were stored and exported as ASCII text file into data processing software (Microsoft Excel complemented with customized code). The non-linearity of the applied force and associated change of deformation has been taken into account numerically. The primary data were converted into stress and true strains (equations 5 and 6). Under oscillatory dynamic loading it is not possible to have true constant static stress as for creep. Changes in dynamic strain (6) also lead to non-uniform static strain (5). For every amplitude value time-point, several oscillation cycles were carried out and thus every data row had locally time-convoluted (i.e. within the single set of oscillations at constant amplitudes) values of dynamic and static parameters (forces, displacements, strains, stresses) for every set of cycles. Note that dynamic and static strains are not independent variables, as both involve instant specimen dimensions.

Obtained in this way pseudo-static and dynamic moduli are shown in Fig. vs. experiment time (lines are added as visual guides) at 25° C. It is seen that these moduli are not constant and thus are not time-invariant measures. A numerical algorithm of time convolution was applied and processed data were non-locally integrated pair-wisely row by row. Resulting values were tabulated in the Microsoft Excel file. For harmonic oscillation used in this example, the functions $f(t)$ in equations (1-4) are eventually true strain (equation 6) and stress, where the stress is time-shifted ahead of strain due to viscoelastic nature of the specimen. By applying the time-convolution to the values and with idempotent analysis, it is possible to obtain alpha-values and viscostiffness for every time-point and deformation-point.

Figure 5:
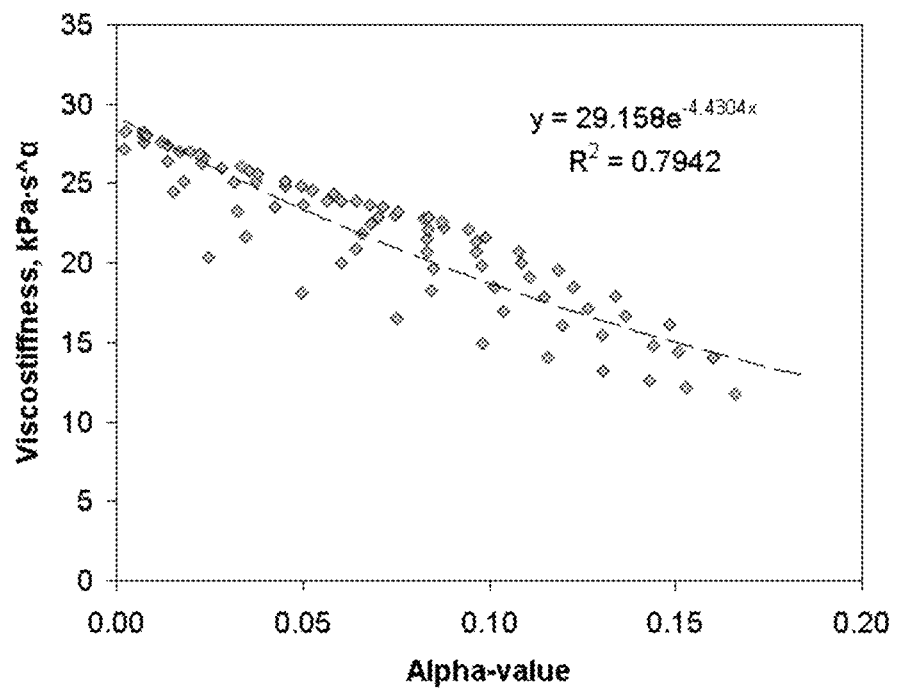
FIG. 5 presents the data for global time-invariant values for the example 2 at 25° C.

These results are shown in FIG. 5 in the form of local time-invariant viscostiffness values vs. respective alpha-values. In the case the specimen would have been ideally linear material, this plot should have approached a straight line. In this example however, it is seen that a non-linearity is present. For generation of global time-invariant parameters for this specimen, the viscostiffness values were extrapolated to zero alpha-value (FIG. 5), as the time-convolution analysis results in an exponential dependence. This results in true intrinsic dynamic modulus of 29.158 kPa, and this value is independent not only on time, but also on the strain or stress, so far strains and stresses remain within the limits of the experiment. In addition, the slope of the curve in FIG. 5 allows calculation of characteristic time and material viscosity values from this intrinsic modulus and the exponent factor. For this specimen the effective viscosity is 347.3 Pa·s and the characteristic time 12 ms.

Figure 4:
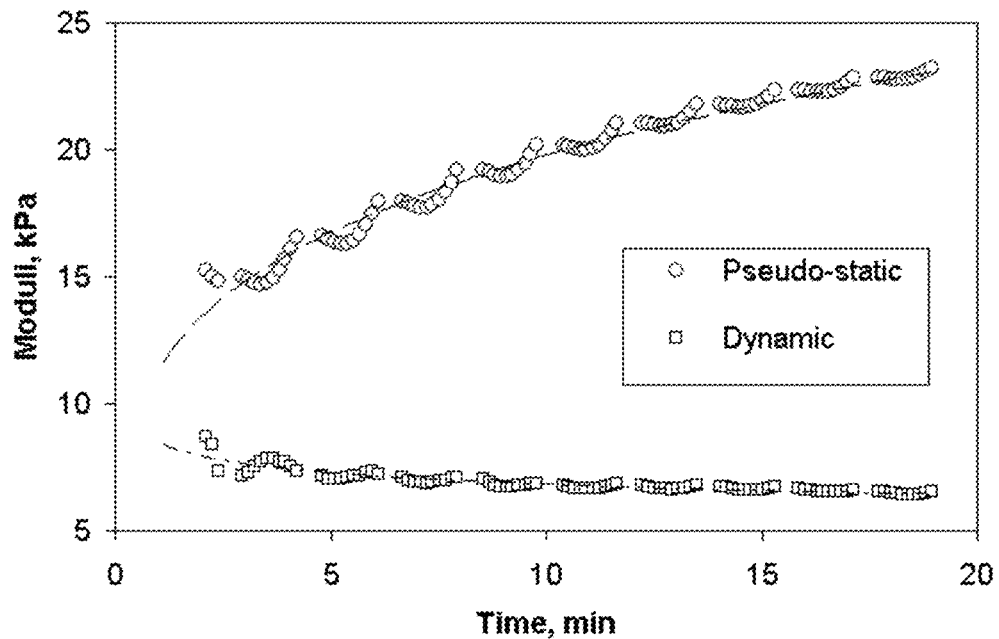
FIG. 4 presents the processed experimental data for the example 2 at 25° C.
Figure 6:
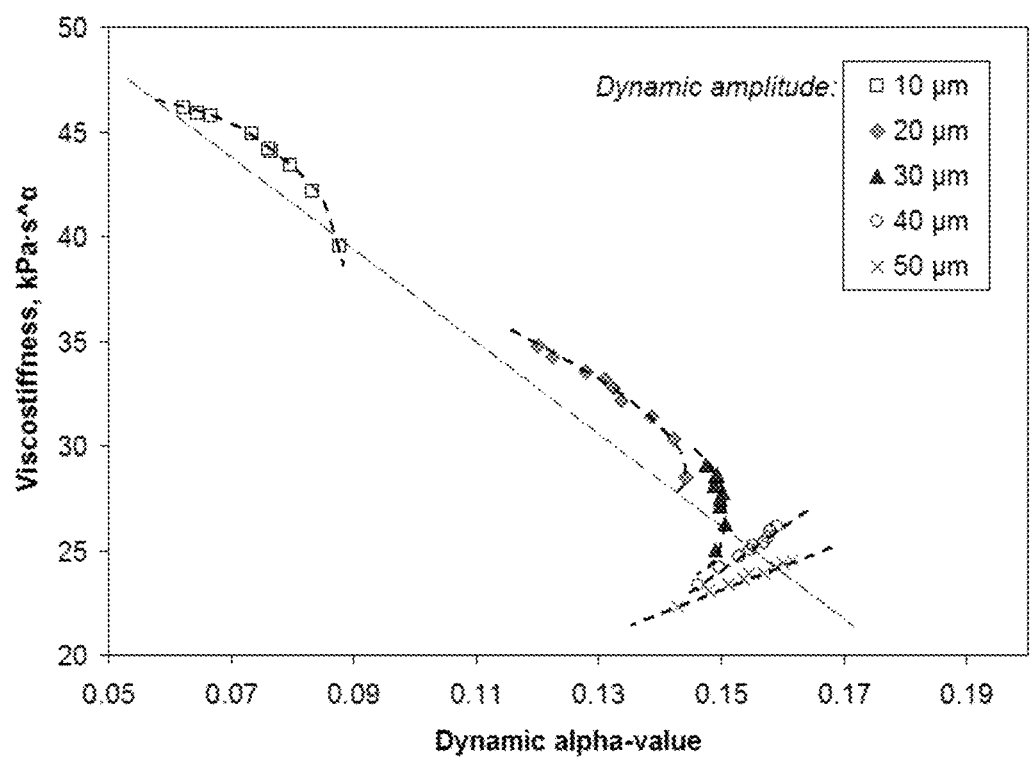
FIG. 6 presents the data of local time-invariant values for the example 2 at 36° C.

The present method allows also a deeper look inside the material behavior than available prior art methods. One may see from FIG. 4 data that at every loading cycle for different amplitudes steps there is a clear non-linear dependence of the moduli vs. displacement. When data are segmented for every cycle separately with the same method as for FIG. 5, viscostiffness function vs. dynamic alpha-value plot is obtained (FIG. 6). These results prove this material has a clear change in the biomechanical behavior when dynamic displacement amplitude at 1 Hz exceeds 30 μm (equivalent to dynamic strain ~0.013). Below this deformation, hydrogel viscostiffness decreases with an increase of alpha-value, but above it goes up when alpha-value becomes higher, even when the global decreasing trend remains. This change indicates fine variations in structural reactivity of the hydrogel subjected to larger mechanical deformation which starts to resist it (increase in the viscostiffness) with simultaneous increase of fluidity (higher alpha-values). Such information is of a great value for development of novel hydrogels, tailoring them to a proper clinical application.

Additional Notes

Unlike prior art biomechanical or combined testing methods known to the inventors, the method of the preferred embodiments is internally consistent and directly related to known laws of physics and mathematics rather than dependent on empirical calibrations, a priori assumptions or on pre-selected material models. In use one thus relies of true experimental outcomes rather than artificial fitting of fragments of separate uncoupled values, being often away for clinical conditions.

The above detailed description together with accompanying drawings shows specific embodiments and examples in which the invention can be practiced. Such examples can include elements in addition to those shown or described. However, the inventors also contemplate examples using any combination or permutation of those elements shown or described (or one or more aspects thereof), either with respect to a particular example (or one or more aspects thereof), or with respect to other examples (or one or more aspects thereof) shown or described herein.

The above description is intended to be illustrative, and not restrictive. Also, in the above detailed description, various features may be grouped together to streamline the disclosure, whereas the inventive subject matter may consist less than all features of a particular disclosed embodiment. Although the present invention has been described in more detail in connection with the above examples, it is to be understood that such detail is solely for that purpose and that variations can be made by those skilled in the art without departing from the spirit of the invention except as it may be limited by the following claims. Thus, the following claims are hereby incorporated into the detailed description, with each claim standing on its own as a separate embodiment, and it is contemplated that such embodiments can be combined with each other in various combinations or permutations.

In this document, the terms "a" or "an" are used, as is common in patent documents, to include one or more than one, independent of any other instances or usages of "at least one" or "one or more." Also, in the following claims, the terms "including" and "comprising" are open-ended, that is, a system, device, article, or process that includes elements in addition to those listed after such a term in a claim are still deemed to fall within the scope of that claim.

Examples shown in the present invention foresee execution of computer instructions operable to configure and run an electronic measuring device to perform these methods as described. An implementation of such instruction can be realized as a code, such as microcode, assembly language code, a higher-level language code, or user-independent executable code (like a computer program product), whether with or without a graphical user interface, stored or properly located on any computer-readable media during execution or at standby.

REFERENCES

1. Lujan T. J., Wirtz K. M., Bahney C. S., Madey S. M., Johnstone B., Bottlang M. A novel bioreactor for the dynamic stimulation and mechanical evaluation of multiple tissue-engineered constructs, Tissue Eng. C 17 (2011), 367-374.
2. Martin I., Wendt D., Heberer M. The role of bioreactors in tissue engineering. Trends in Biotechnol. 22 (2004), 80.
3. Bioreactor systems for tissue engineering II: strategies for the expansion and directed differentiation of stem cells, Eds. C. Kasper, M. van Griensven, R. Pörtner; in "Advances in Biochemical Engineering/Biotechnology", Springer, Vol. 123 (2010), 330 P.
4. Hutmacher D. W., Singh H. Computational fluid dynamics for improved bioreactor design and 3D culture. Trends in Biotechnol. 26 (2008), 166-172.
5. Pioletti D. P., Muller J., Rakotomanana L. R., Corbeil J., Wild, E. Effect of micromechanical stimulations on osteoblasts: development of a device simulating the mechanical situation at the bone-implant interface. J. Biomech. 36 (2003), 131-135.
6. Shimomura K., Kanamoto T., Kita K., Akamine Y., Nakamura N., Mae T., Yoshikawa H., Nakata K. Cyclic compressive loading on 3D tissue of human synovial fibroblasts upregulates prostaglandin $E_2$ via COX-2 production without IL-1β and TNF-α. Bone Joint Res. J. 3 (2014), 280-288.
7. Mauck R. L., Soltz M. A., Wang C. C. B., Wong D. D., Chao P. G., Valhmu W. G., Hung C. T., Atesian G. A. Functional tissue engineering of articular cartilage through dynamic loading of chondrocyte-seeded agarose gels. Trans. ASME, 122 (2000), 252-260.
8. Salvetti D. J., Pino C. J., Manuel S. G., Dallmeyer I., Rangarajan S. V., Meyer T., Kotov M., Shastri V. P. Design and validation of a compressive tissue stimulator with high-throughput capacity and real-time modulus measurement capability. Tissue Eng. C 18 (2012), 205-214.
9. Mohanraj B., Hou C., Meloni G. R., Cosgrove B. D., Dodge G. R., Mauck R. L. A high-throughput mechanical screening device for cartilage tissue engineering. J. Biomech. 47 (2014), 2130-2136.
10. DeAlmeida M. F., Ferreira L. C. F. Self-similarity, symmetries and asymptotic behavior in Morrey spaces for a fractional wave equation. Differ. Integr. Equ. 25 (2012), 957-976.
11. Verotta D. Fractional dynamics pharmacokinetics-pharmacodynamic models. J. Pharmacokinet. Pharmacodyn. 37 (2010), 257-276.
12. Hanyga A., Seredynska M. Power-law attenuation in acoustic and isotropic anelastic media. Geophys. J. Inter. 155 (2003), 830-838.
13. Maslov V. The characteristics of pseudo-differential operators and difference schemes. Actes Congrès intern. Math. 2 (1970), 755-769.
14. Marquez J. P., Genin G. M., Zahalak G. I., Elsony E. L. Thin bio-artificial tissues in plane stress: the relationship between cell and tissue strain, and an improved constitutive model. Biophys. J. 88 (2005), 765-777.
15. Baeumer B., Satoko K., Meerschaert M. M. Inhomogeneous fractional diffusion equations. Frac. Calc. Appl. Anal. 8 (2005), 371-386.
16. Gorenflo R., Luchko Y., Mainardi, F. Analytical properties and applications of the Wright function. Frac. Calc. Appl. Anal. 2 (1999), 383-414.
17. Gerisch A., Chaplain M. A. J. Robust numerical methods for taxis-diffusion-reaction systems: applications to biomedical problems. Mathem. Computer Model. 43 (2006), 49-75.
18. Gunawardena J. An introduction to idempotency. HP Laboratories Bristol, Publication HPL-BRIMS-96-24 (1996), 50 p.
19. Luchko Y., Mainardi F. Cauchy and signaling problems for the time-fractional diffusion-wave equation. J. Vibr. Acoust. 136 (2014), 050904.
20. Norris A. Eulerian conjugate stress and strain. J. Mech. Mater. Struct. 3 (2008), 243-260.
21. Lubarda V. A., Chen M. C. On the elastic moduli and compliances of transversely isotropic and orthotropic materials. J. Mech. Mater. Struct. 3 (2008), 155-170.
22. Xiao H. Invariant characteristic representations for classical and micropolar anisotropic elasticity tensors. J. Elasticity 40 (1995), 239-265.
23. Verbruggen S. W., Vaughan T. J., McNamara L. M. Fluid flow in the osteocyte mechanical environment: a fluid-structure interaction approach. Biomech. Model Mechanobiol. 13 (2014), pp. 85-97.
24. Huiskes R., Ruimerman R., Van Lenthe G. H., Janssen J. D. Effects of mechanical forces on maintenance and adaptation of form in trabecular bone. Nature 405 (2000), 704-706.
25. Claes L. E., Heigele C. A. Magnitudes of local stress and strain along bony surfaces predict the course and type of fracture healing. J. Biomechanics 32 (1999), 255-266.
26. Milan J. L., Planell J. A., Lacroix D. Simulation of bone tissue formation within a porous scaffold under dynamic compression. Biomech. Model. Mechanobiol. 9 (2010), 583-596.

27. Sittichokechaiwut A., Edwards J. H., Scutt A. M., Reilly G. C. Short bouts of mechanical loading are as effective as dexamethasone at inducing matrix production by human bone marrow mesenchymal stem cells. Europ. Cells Mater. 20 (2010), 45-57.
28. Sladkova M., de Peppo G. M. Bioreactor systems for human bone tissue engineering. Processes 2 (2014), 494-525.

What is claimed is:

1. A method for determining a plurality of time-invariant functional properties of materials in a high-output screening, said method comprising the steps of:
   a) positioning a material specimen, selected from the group consisting of a biomaterial, a tissue sample, a live matter containing material, and a pharmaceutical substance, or any combination thereof, onto a sample holder absent explicit fixation of the specimen;
   b) immersing the specimen and the sample holder into a fluid;
   c) establishing a contact of the specimen with a sensor probe;
   d) applying a non-destructive mechanical stimulus, selected from the group consisting of a bending, a compressing, a shearing, and ultrasonic waves, to the specimen via the sensor probe, said stimulus inducing a movement of the fluid adjacent to the specimen;
   e) measuring via the sensor probe changes in a signal, reflecting changes in dimensions of the specimen, as a function of time and applied stimulus parameters;
   f) subtracting signal contributions from background sources, including the sample holder, the sensor probe and the measurement parts themselves,
   g) processing the measured data after step f) by time convolution in a material model free assumptions manner; and
   h) calculating the specimen time-invariant material properties, selected from the group consisting of an aggregate modulus, a specimen viscosity, an intrinsic modulus, a permeability, a permittivity, a slope modulus, a dynamic modulus, a dimensionless alpha-value, a visco-stiffness, a fluid diffusivity, a specimen loading history, and characteristic times, from the processed data.

2. The method of claim 1, wherein the method additionally comprises a step for comparing results of step h) with corresponding results of a reference or a control specimen.

3. The method of claim 1, wherein the time-invariant functional properties determined are further correlated with presence or concentration of chemical species, presence or status of live species or changes thereof, either separately or in a combination.

4. The method of claim 1, wherein the method is used to evaluate swelling and swelling pressure of the specimen under controlled conditions.

5. The method of claim 1, wherein permeability and permittivity of the material are evaluated free of application of the fluid pressure gradient from an external source.

6. The method of claim 1, wherein the method it is used to evaluate kinetics of possible chemical, biochemical or biological reactions between the specimen and the surrounding fluid media or with additions to this media.

7. A computer product embodied on a computer readable storage medium, the computer program product comprising instructions executable by one or more processors to determine a plurality of time-invariant functional properties of materials in high-output screening, wherein the computer program product comprises instructions to:
   analyze an experimental data file obtained from the method of claim 1;
   parse the experimental data into prepared data;
   convert the parsed data into working variables;
   segment the working variables by experiment time, frequency, stress, true strain, etc. parameters depending on mode of loading and sample holder layout;
   process the variables by iterative time convolution;
   execute idempotent analysis onto working variables;
   check quality and errors of the procedure and re-iterate; and
   calculate true time-invariant variables from idempotent analysis.

* * * * *